(12) United States Patent
Oelofse

(10) Patent No.: US 12,083,272 B2
(45) Date of Patent: Sep. 10, 2024

(54) MULTI-PERSON MEDICAL VENTILATOR

(71) Applicant: Rudolph Oelofse, McClellan, CA (US)

(72) Inventor: Rudolph Oelofse, McClellan, CA (US)

( * ) Notice: Subject to any disclaimer, the term of this patent is extended or adjusted under 35 U.S.C. 154(b) by 444 days.

(21) Appl. No.: 17/220,859

(22) Filed: Apr. 1, 2021

(65) Prior Publication Data

US 2021/0308397 A1    Oct. 7, 2021

Related U.S. Application Data

(60) Provisional application No. 63/003,861, filed on Apr. 1, 2020.

(51) Int. Cl.
*A61M 16/00* (2006.01)
*A61L 9/20* (2006.01)
*A61M 16/20* (2006.01)

(52) U.S. Cl.
CPC ........... *A61M 16/0075* (2013.01); *A61L 9/20* (2013.01); *A61M 16/208* (2013.01); *A61L 2209/12* (2013.01); *A61M 2202/0208* (2013.01)

(58) Field of Classification Search
CPC ............ A61M 16/0075; A61M 16/208; A61M 2202/0208; A61M 16/0084; A61M 2016/003; A61M 2205/103; A61M 2205/3334; A61M 2209/084; A61M 2209/10; A61M 16/125; A61M 16/201; A61M 16/1005; A61M 2205/08; A61L 9/20; A61L 2209/12; F04B 43/084–088; F04B 45/02–027

See application file for complete search history.

(56) References Cited

U.S. PATENT DOCUMENTS

| | | | | |
|---|---|---|---|---|
| 2,423,875 A * | 7/1947 | Curtis | ...................... | G01F 23/52 |
| | | | | 73/304 R |
| 3,128,764 A * | 4/1964 | Koehn | ................... | A61M 16/18 |
| | | | | 128/204.13 |
| 3,890,967 A * | 6/1975 | Elam | ...................... | A61M 16/00 |
| | | | | 92/39 |
| 4,452,241 A * | 6/1984 | Sarnoff | ............. | A61M 16/0833 |
| | | | | 128/205.13 |
| 5,965,089 A * | 10/1999 | Jarvik | .................. | A61M 1/3656 |
| | | | | 604/6.11 |
| 2010/0083965 A1* | 4/2010 | Virr | ........................ | A61M 16/06 |
| | | | | 128/203.26 |

* cited by examiner

*Primary Examiner* — Michael R Reid
*Assistant Examiner* — Tina Zhang
(74) *Attorney, Agent, or Firm* — Mark A. Pitchford; Eric B. Fugett; Pitchford Fugett, PLLC

(57) ABSTRACT

A ventilator uses teeth of gear to operate up to eight or more bellows. A common drive shaft can be used to operate a stack of multiple such gears, which collectively operate up to 40 or more bellows. Valves can be used to control flow from different ones of the bellows to individual recipients.

8 Claims, 7 Drawing Sheets

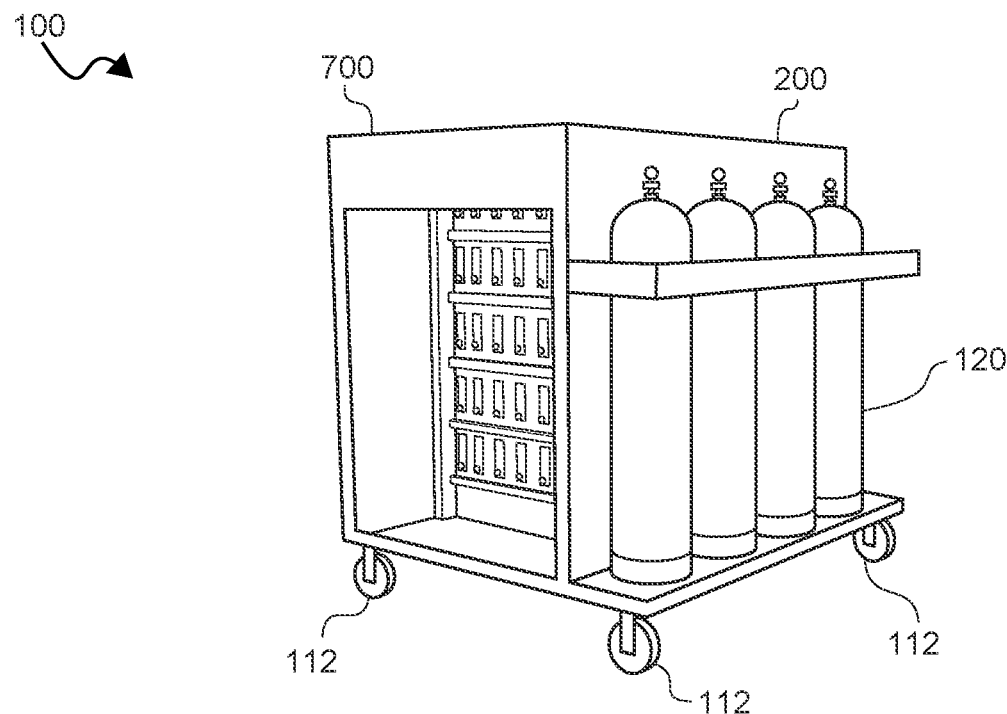
Figure 1
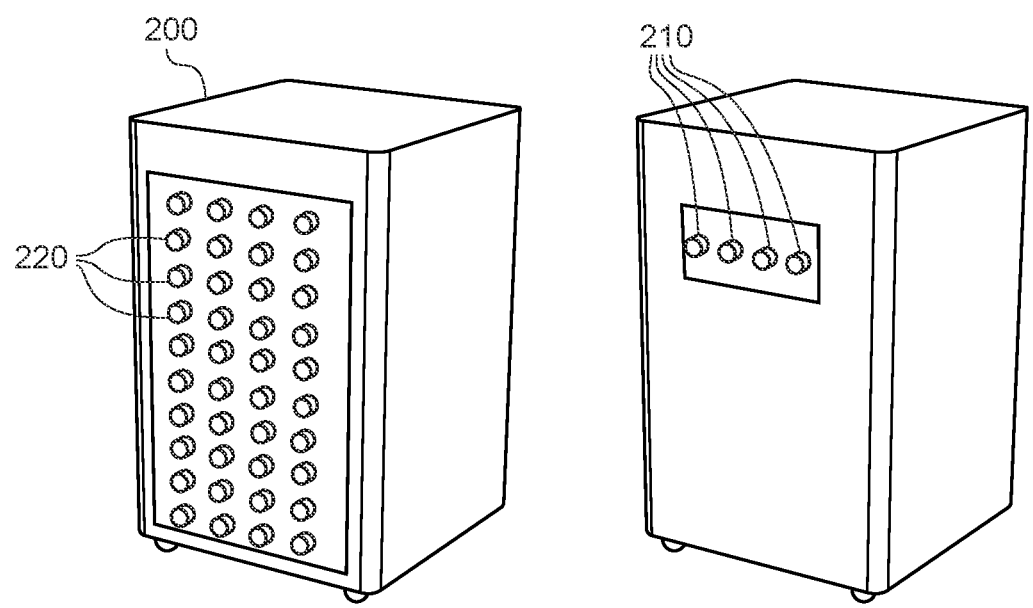 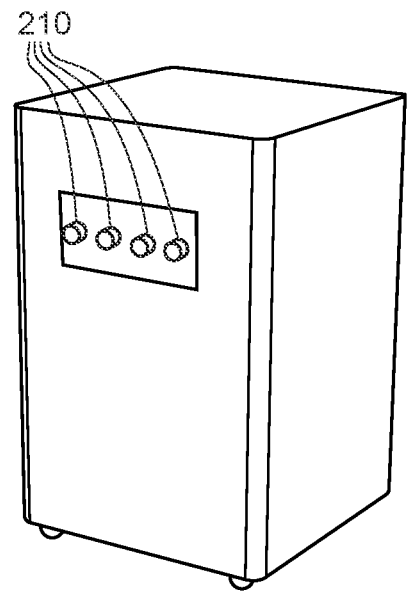
Figure 2A          Figure 2B

MULTI-PERSON MEDICAL VENTILATOR

PRIORITY CLAIM

This application claims the benefit of U.S. provisional application Ser. No. 63/003,861, filed Apr. 1, 2020. The '861 application, and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is medical ventilators.

BACKGROUND

The background description includes information that may be useful in understanding the present invention. It is not an admission that any of the information provided herein is prior art or relevant to the presently claimed invention, or that any publication specifically or implicitly referenced is prior art.

Amid the pandemic coronavirus outbreak in 2020, one of the biggest problems is the lack of ventilators to support patients who are experiencing serious breathing difficulties. A ventilator is a machine that can help a person breathe by delivering oxygen through a tube placed in the mouth or nose, or through a hole in the front of the neck. In a normal circumstance, each patient receives his/her own ventilator. However, because of insufficient supply, hospitals sometimes even experiment with having two or even four patients share a single air supply having multiple patient ports. See e.g., https://www.livescience.com/coronavirus-emergency-ventillator-capacity-increase.html). Such use is not approved by the Food and Drug Administration (FDA), and carries significant medical risks.

Thus, there is still a need for a ventilator machine that can support multiple patients with individual air supplies, and is preferably easy to operate and relatively inexpensive.

SUMMARY OF THE INVENTION

The inventive subject matter provides apparatus, systems and methods in which a ventilator is capable of proving respiratory support to at least two people.

In preferred embodiments, a multiple-person ventilator provides breathable air to two or more individuals, with a bellow corresponding to each individual disposed within a ventilator cabinet. Each bellows has its own input and output valves, and intermittently pumps breathable oxygen or oxygenated gas to corresponding a gas line.

Bellows are preferably arranged in multiple levels, with numerous bellows on each level arranged about a central gear. The gears of the different levels are preferably rotated by a common drive shaft. Up to eight, or even more bellows can be accommodated on any given level, and there can be up to five or more levels of bellows. A primary motor and preferably a backup motor deliver power to each of the gears through the common drive shaft. Alternatively, different levels of bellows can be driven by different motors.

A pumping cabinet can advantageously be used to receive oxygen from a compressed oxygen source, and house the gear(s) and bellows. Atmospheric air can optionally be added to the oxygen within the pumping cabinet.

A distribution cabinet is preferably outfitted with individual flow valves and meters for each gas line, such that flow can be individually controlled. The flow valves can be manually operated using a knob or other manual control, and the meters can be ball flow meters configured to meter gas flowing through corresponding the gas lines.

UV light can be configured to irradiate gas passing from the bellows to individual patients through the gas lines.

The oxygen and distribution cabinets can each have wheels to facilitate portability. In other embodiments, the pumping cabinet and distribution cabinet can be supported by a common set of wheels.

The inventive subject matter further includes a method of providing concurrent ventilation to multiple patients, having steps of (1) rotating a first gear having at least one tooth; (2) using the at least one tooth to operate at least first and second bellows, to pump air into at least first and second gas lines, respectively; (3) supplying compressed oxygen to supply oxygen to inlets of the first and second bellows; and (4) independently adjusting flow through the first and second gas lines.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 is a perspective view of a ventilator system, generally comprising a pumping cabinet and a distribution cabinet.

FIG. 2A is a perspective view of the front of a pumping cabinet ventilator system of FIG. 1, showing output connectors.

FIG. 2B is a perspective view of the back of the pumping cabinet of FIG. 1, showing input connectors.

DETAILED DESCRIPTION

Figure 3:
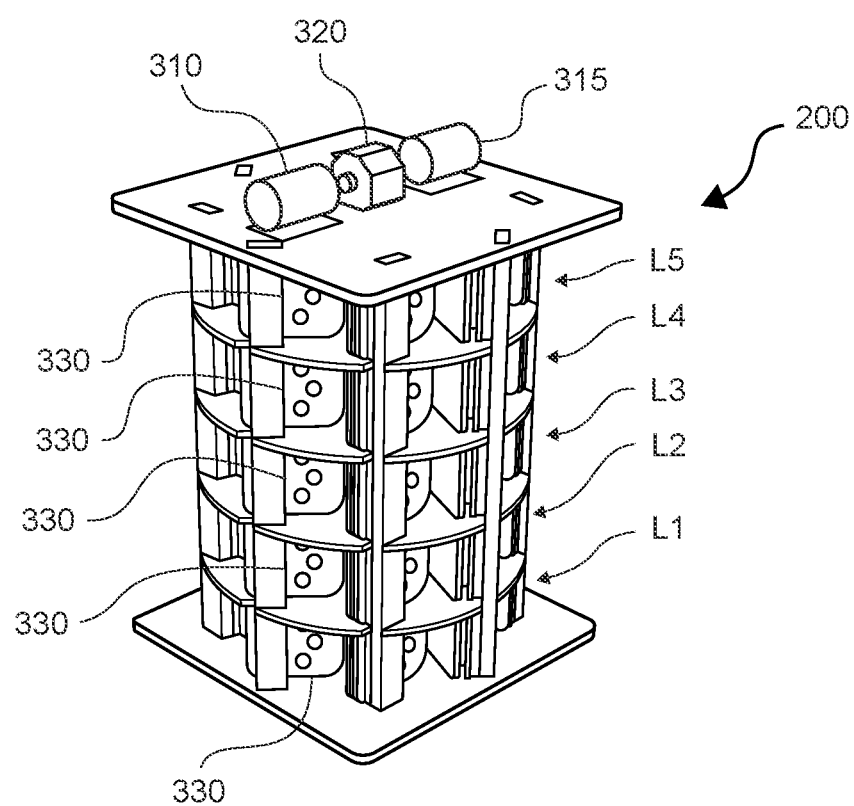
FIG. 3 is a perspective view of the pumping cabinet of FIGS. 2A. 2B, with side walls removed to depict multiple levels of bellows.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The recitation of ranges of values herein is merely intended to serve as a shorthand method of referring individually to each separate value falling within the range. Unless otherwise indicated herein, each individual value is incorporated into the specification as if it were individually recited herein.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

FIG. 1 is a perspective view of a ventilator system 100, generally comprising a pumping cabinet 200, a distribution cabinet 700, and one or more compressed gas tanks 120.

Typically the compressed gas tanks 120 provide substantially pure oxygen to the pumping cabinet 200 via a manifold (not shown). Multiple compressed gas tanks are preferably used serially, so that expired tanks can be replaced with full tanks, without interfering with functioning of the device. Alternatively, two or more of the tanks could be used in parallel.

Ventilator system 100 is configured to simultaneously support up to 40 patients with fresh, UV-sterilized, oxygen through individual air lines 150 for each patient. As discussed below, other contemplated embodiments provide greater or fewer air lines. Despite being able to support a large number of lines to individual patients, the system is modular and simple, and as such it requires little technical training to repair and maintain.

Castor wheels 112 provide mobility to the ventilator system 100. Ventilator system 100 is preferably sized and dimensioned such that it can be moved about by two people, and placed at a distance from patients to help prevent contamination. In some embodiments, the ventilator system 100 can be configured to fit into escalators, and through Americans with Disabilities Act (ADA) accessible doorways.

FIGS. 2A and 2B are front and back views, respectively, of pumping cabinet 200. Multiple input connectors 210 is positioned on a back wall of pumping cabinet 200, passing oxygen from the one or more external oxygen tanks 120 to the inside of pumping cabinet 200. Numerous output connectors 220 are positioned on a front wall of pumping cabinet 200, corresponding to the number of bellows 300 (see FIGS. 3, 4A, 4B, 5A, 5B) in the ventilator system 100.

In preferred embodiments, the pumping cabinet 200 is made of a strong but lightweight material, including for example fiber-reinforced polymer or fiberglass, ceramic matrix composites, metal matrix composites, and other advanced composite materials.

FIG. 3 is a perspective view of pumping cabinet 200, with side walls removed to depict multiple levels L1, L2, L3, L4, L5 of bellows 330. In some embodiments, the pumping cabinet 200 completely shields the ventilator cabinet from atmospheric air, such that only oxygen, or whatever mixture of gas is being provided by the compressed gas tanks 120, is pumped by the bellows 330. In other embodiments, an auxiliary pump (no charge) can be used to pump atmospheric air into the pumping cabinet 200.

At least one electric motor 310, and optionally one backup motor 315, rotates a drive shaft (see FIG. 4B), which in turn rotates a gear at each of the levels L1, L2, L3, L4, L5. Rotation of the gears operates the bellows. A gear box 320 is employed to transmit power from the primary motor 310 and backup motor 315, to the drive shaft 435. Gear box 320 is preferably configured such that if primary motor 310 fails, then backup motor 315 can continue operating, and primary motor 310 can be replaced without shutting the system down.

Figure 4A:
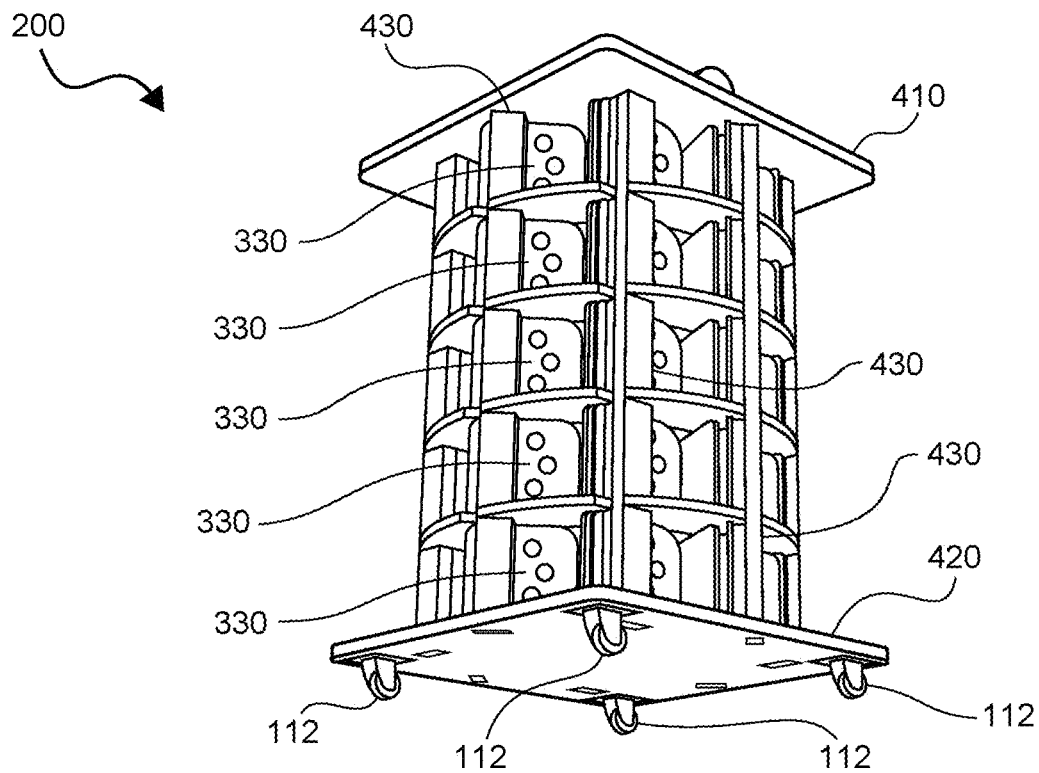
FIG. 4A is another additional perspective view of the pumping cabinet of FIG. 2, with side walls removed.
Figure 4B:
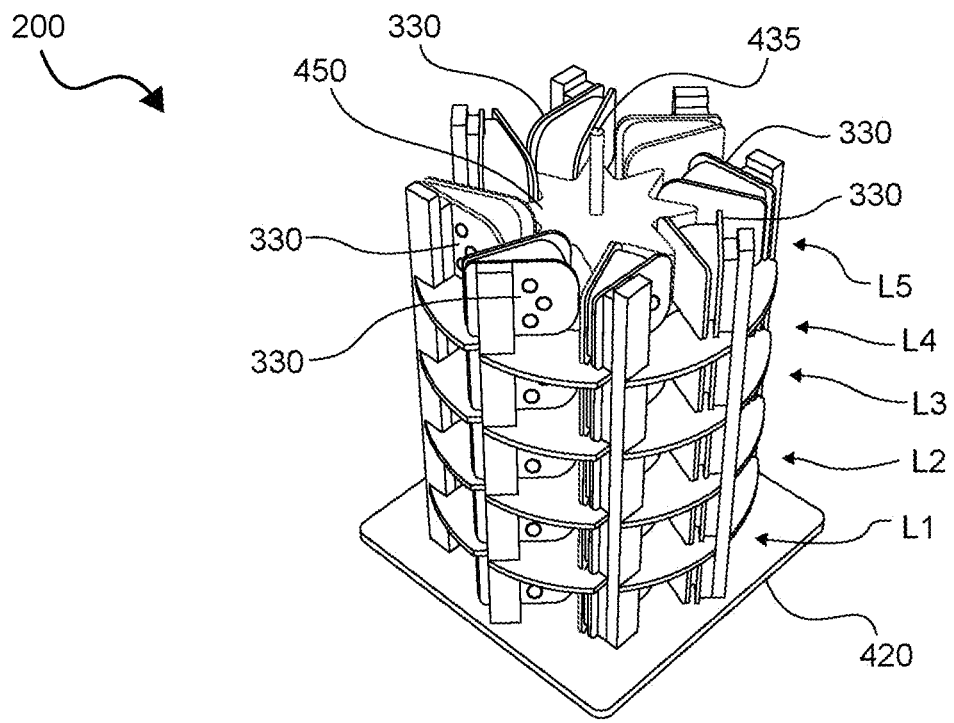
FIG. 4B is another additional perspective view of the pumping cabinet of FIG. 2, with both the side walls and the top removed.

FIGS. 4A and 4B show bellows 330 of FIG. 3 from different perspectives. There is a top 410 and a bottom 420, with wheels 112 supporting the bottom 420. The top and bottom are coupled by struts 430. FIG. 4B depicts the drive shaft 435 and one of the gears 450 on level L5. Eight bellows 330 are positioned about gear 450, such that rotation of gear 450 operates the bellows 330. FIGS. 4A and 4B should read as having substantially identical gears 450 and bellows 330 on levels L1-L5.

Although level L5 in FIG. 4B depicts eight bellows 450 on each level, it is contemplated that other embodiments could have a greater or lesser number of bellows (preferably 2-14) on any given level. It is also contemplated that other embodiments could have a greater or lesser number of levels (preferably 2-10). It is further contemplated that the gears of different levels could be driven by different motors.

Figure 5A:
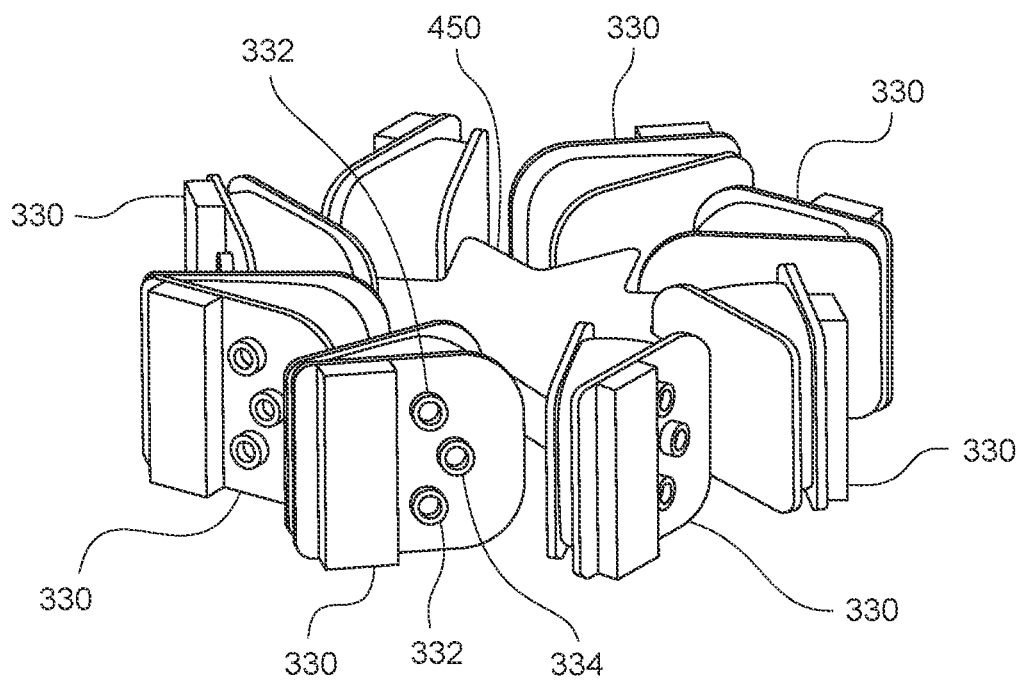
FIG. 5A is a perspective view of the bellows and gear of level L5.
Figure 5B:
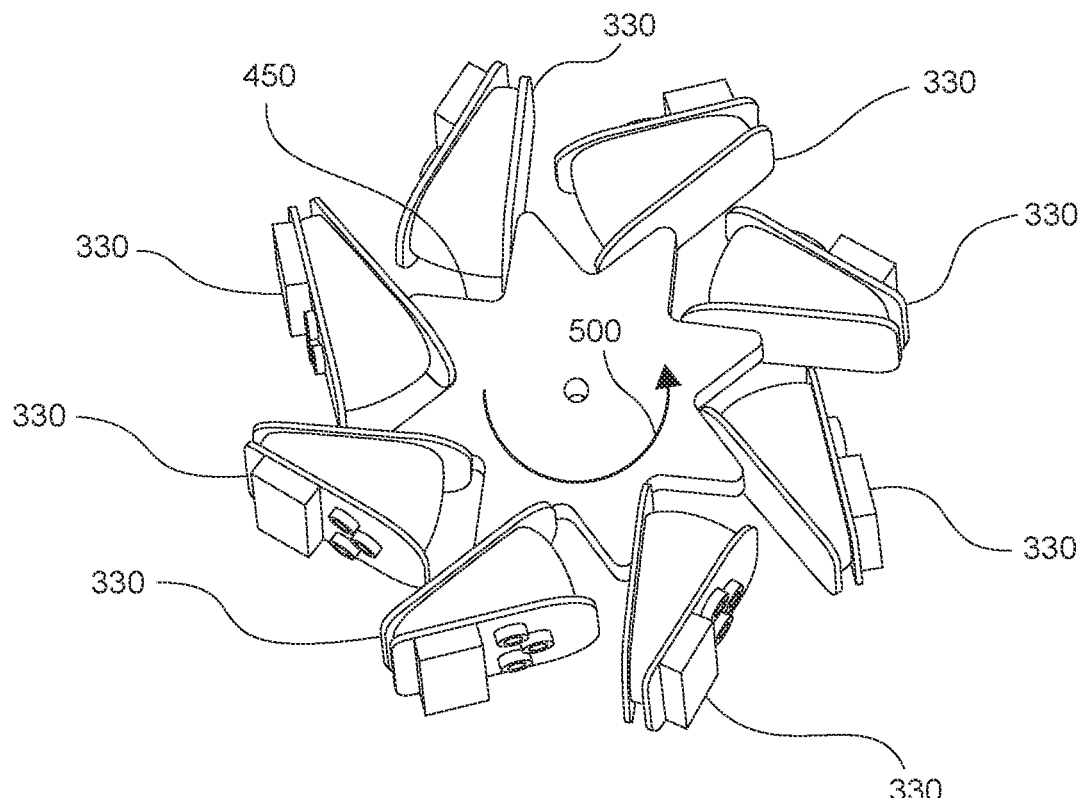
FIG. 5B is another perspective view of the bellows and gear depicted in FIG. 5A.

FIGS. 5A and 5B are perspective views of the bellows and gear of level L5. There are eight bellows 330, all driven by gear 450. Each of the bellows 330 has two gas inlets 332 and one gas outlet 334. The gas inlets 332 and gas outlets 334 are one-way valves. As the gear 450 rotates in the direction of arrow 500, a cavity within each of the bellows 330 is sequentially expanded and compressed, forcing gas out through the gas outlets. In other contemplated embodiments there can be different numbers of gas inlets and outlets.

As depicted in FIGS. 5A and 5B, all of the bellows 330 of level L5 operate synchronously, so that gas is pumped out through each of the outlets 334 at the same time. This is a function of the even spacing of the teeth about the perimeter of gear 450. It is also contemplated that the teeth of a given gear could be arranged so that the corresponding bellows operate asynchronously (not shown), and therefore pump at different times. However, that arrangement reduces the number of bellows that can be positioned about a given gear.

In a more efficient arrangement, the positional rotation of the gears 450 relative to the bellows at the different levels would be offset from one another by an amount that causes the bellows on the different levels to operate the bellows asynchronously, even though the bellows on any given level would all operate synchronously. Such a design evens out the strain against the motor(s) at any given time. For example, if each level has eight bellows evenly spaced about a gear, pumping cycle for each of the bellows takes place over 45° of gear rotation. To even out the strain against the motor(s) 310, 315, the gears of each of levels L5-L2 in the five level ventilator system 100 is should be interpreted as being offset from the gear of the level below it by 7° (45°÷5), and thereby provide asynchronous operation of each of the bellows 330. If there were only three levels, each having eight bellows, then the gears on each of levels L3-L2 could advantageously be offset from the gear of the level below it by 15° (45°÷3).

Those of ordinary skill in the art will appreciate that the positional rotation of the gears 450 relative to the bellows at the different levels can be offset be differential the position of the gears on the different levels, and/or differential positioning of the bellows on the different levels. All such differential positioning can effect asynchronous operation of the bellows, ant thereby reduce the strain on the motor(s).

Figure 6:
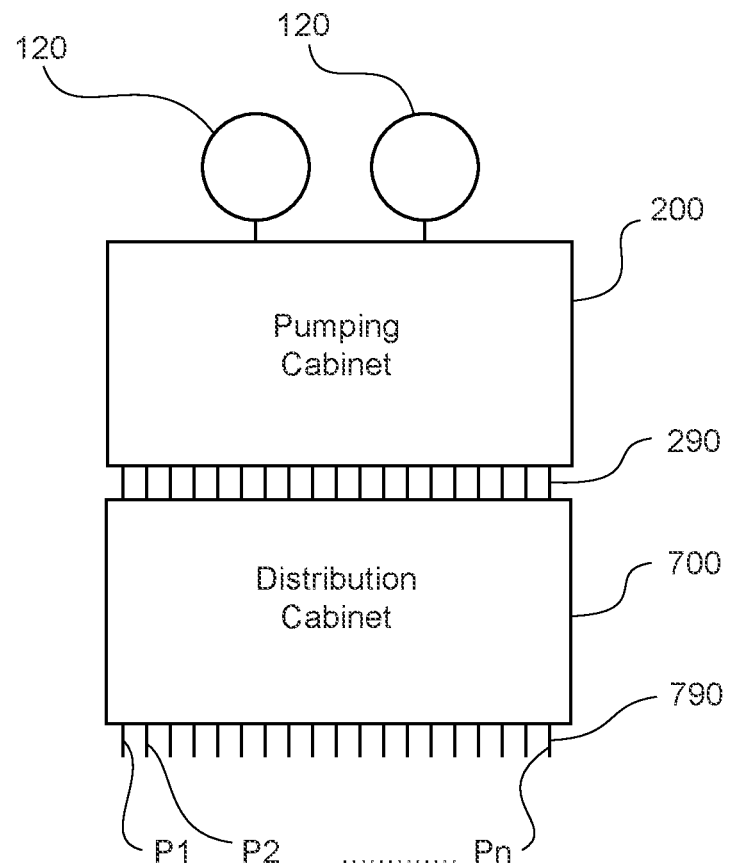
FIG. 6 is a schematic of the ventilator system of FIG. 1, in which oxygen flows sequentially from oxygen tanks to a pumping cabinet to a distribution cabinet with valves and flow meters, and thence to individual patients.

FIG. 6 shows a schematic of gas flow in the external view of a sterilization and flow control cabinet disposed in the ventilation system 100 of FIG. 1. Oxygen flows sequentially from oxygen tanks 120 into the pumping cabinet 200, then through multiple gas lines 290 into a distribution cabinet 700, then out through multiple patient gas lines 790 to patients P1-Pn.

Figure 7:
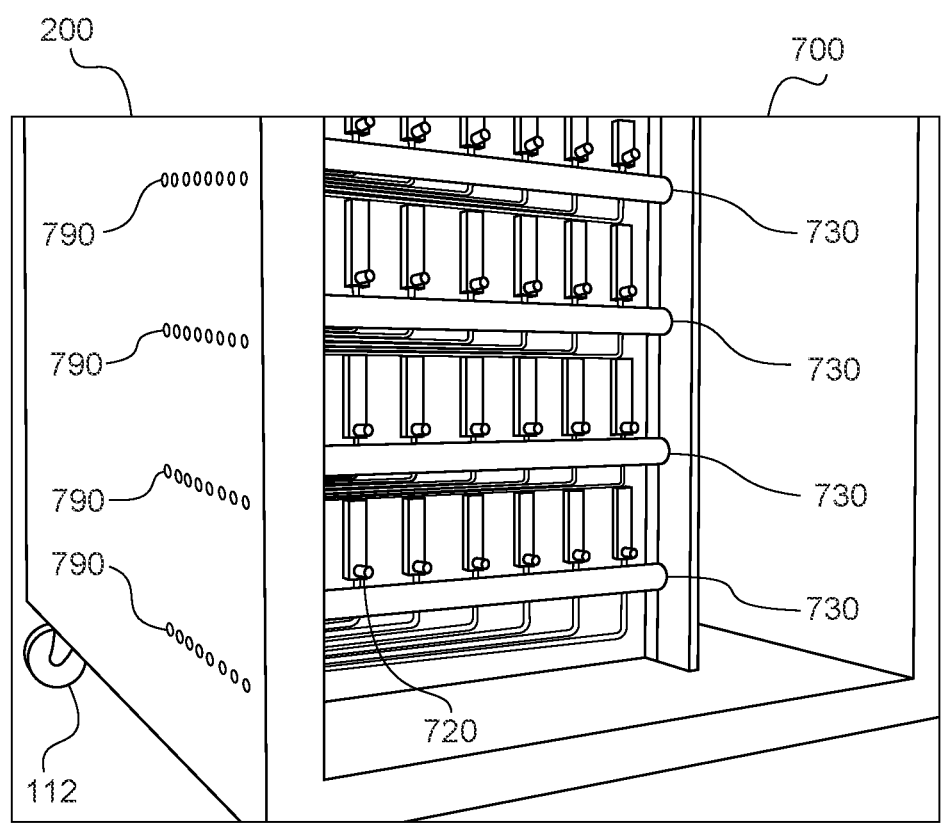
FIG. 7 is a perspective cutoff view of the distribution and pumping cabinets of FIG. 1.

In FIG. 7, distribution cabinet 700 generally includes outlets 710 for distribution of gas to patients, individual ball valve controls 720 having manually operable knobs 721, configured to regulate flow out of the outlets 710, and UV light bars 730 for sterilizing gas flowing to the outlets 710. The ball valve controls 720 operate as gas flow meters.

Figure 8:
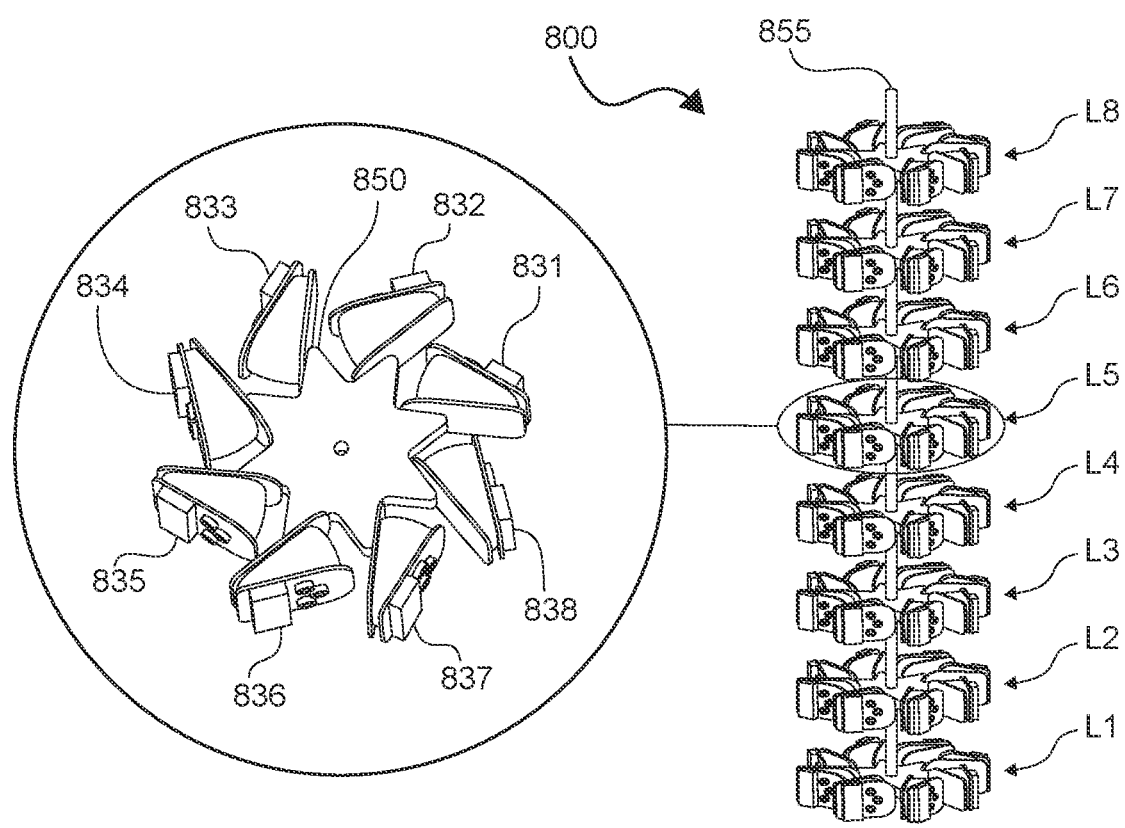
FIG. 8 is a perspective view of an alternative ventilation system having a stack of eight levels of bellows and gears, all operated by the single drive shaft.

FIG. 8 is a perspective view of a stack 800 of eight levels (L1-L8), each of which has eight bellows 831-838 (substantially identical to bellows 830 in FIGS. 3, 4A-4B, and 5A-5B), and gears 850 (substantially identical to gears 350 in FIGS. 3, 4A-4B, and 5A-5B). Each of gears 850 are driven by drive shaft 855. Stack 800 is part of an alternative ventilator system, the remainder of which is not shown, but other than the greater number of layers, would be substantially configured as that shown the other figures. This arrangement provides 56 individual lines of gas.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A multiple-person ventilator for providing breathable air to at least first and second patients, said multiple-person ventilator comprising:
   first and second bellows disposed within a bellows cabinet, which is configured to intermittently pump breathable gas to first and second gas lines, respectively, wherein the first and second bellows are operated by teeth of a first gear; and
   at least third and fourth, fifth and sixth, seventh and eighth bellows operated by the first gear.

2. The ventilator of claim 1, wherein the third and fourth bellows intermittently pump breathable gas to third and fourth gas lines.

3. The ventilator of claim 1, further comprising at least second, third, fourth, and fifth gears configured to collectively operate a total of at least 40 bellows.

4. The ventilator of claim 1, wherein the first bellows has at least two one-way input valves.

5. The ventilator of claim 1, further comprising a UV light source configured to irradiate gas passing through at least the first gas line.

6. The ventilator of claim 1, further comprising a distribution cabinet having first and second flow valves configured to control gas flowing through the first and second gas lines, respectively.

7. The ventilator of claim 6, wherein the first and second flow valves are configured to be manually operated.

8. The ventilator of claim 6, further the distribution cabinet has first and second ball flow meters configured to meter gas flowing through the first and second gas lines, respectively.

* * * * *